United States Patent [19]

Singer et al.

[11] Patent Number: 5,294,433

[45] Date of Patent: Mar. 15, 1994

[54] USE OF H-2 ANTAGONISTS FOR TREATMENT OF GINGIVITIS

[75] Inventors: Robert E. Singer, Fairfield; James P. Ebel, Cincinnati, both of Ohio

[73] Assignee: The Procter & Gamble Company, Cincinnati, Ohio

[21] Appl. No.: 19,782

[22] Filed: Mar. 5, 1993

Related U.S. Application Data

[63] Continuation-in-part of Ser. No. 868,805, Apr. 15, 1992.

[51] Int. Cl.$^5$ .......................... A61K 7/16; A61K 7/18; A61K 7/22
[52] U.S. Cl. ...................................... 424/52; 424/49; 424/54
[58] Field of Search ............... 514/399, 406, 900, 902; 424/52, 54

[56] References Cited

U.S. PATENT DOCUMENTS

| | | | |
|---|---|---|---|
| 3,574,859 | 4/1971 | Kosti | 424/330 |
| 3,822,349 | 7/1974 | Kosti | 424/54 |
| 3,832,460 | 8/1974 | Kosti | 424/54 |
| 3,839,522 | 10/1974 | Kosti | 424/54 |
| 3,950,333 | 4/1976 | Durant et al. | 260/250 A |
| 4,128,658 | 12/1978 | Price et al. | 424/285 |
| 4,256,743 | 3/1981 | Goldhaber | 424/247 |
| 4,283,408 | 8/1981 | Hirata et al. | 424/270 |
| 4,293,557 | 10/1981 | Shibata et al. | 424/267 |
| 4,375,547 | 3/1983 | Pioch | 548/205 |
| 4,386,099 | 5/1983 | Cereda et al. | 424/273 R |
| 4,419,352 | 12/1983 | Cox et al. | 424/248.4 |
| 4,569,837 | 2/1986 | Suzuki et al. | 424/28 |
| 4,572,832 | 2/1986 | Kigasawa et al. | 424/19 |
| 4,585,790 | 4/1986 | Padfield et al. | 514/471 |
| 4,933,182 | 6/1990 | Higashi et al. | 424/435 |
| 4,952,402 | 8/1990 | Sparks et al. | 424/419 |
| 5,023,082 | 6/1991 | Friedman et al. | 424/426 |
| 5,053,032 | 10/1991 | Barclay et al. | 604/892.1 |
| 5,102,666 | 4/1992 | Acharya | 424/487 |
| 5,110,605 | 5/1992 | Acharya | 424/487 |
| 5,188,839 | 2/1993 | Pearmain | 424/464 |
| 5,200,194 | 4/1993 | Edgren et al. | 424/473 |
| 5,200,195 | 4/1993 | Dong et al. | 424/473 |
| 5,221,688 | 6/1993 | Clitherow et al. | 514/400 |

FOREIGN PATENT DOCUMENTS

| | | | |
|---|---|---|---|
| 950833 | 7/1974 | Canada . | |
| 0241179 | 10/1987 | European Pat. Off. | A61K 9/70 |
| 0256566 | 2/1988 | European Pat. Off. | A61K 7/26 |
| 0349657 | 1/1990 | European Pat. Off. | A61K 31/55 |
| 4-89428 | 3/1992 | Japan | A61K 31/13 |
| 89/04178 | 5/1989 | PCT Int'l Appl. | A61K 45/06 |
| 1045031 | 10/1966 | United Kingdom | A61K 7/16 |

OTHER PUBLICATIONS

Ash; A. S. F. & H. O. Schild, "Receptors mediatiing Some Actions of Histamine", Brit. J. Pharmacol. Chemother., vol. 27 (1966), pp. 427–439.

Black, J. W., W. A. M. Duncan, C. J. Durant, C. R. Ganellin & E. M. Parsons, "Definition and Antagonism of Histamine $H_2$–Receptors", Nature, vol. 236 (Apr. 21, 1972), pp. 385–390.

Dews, P. B. & J. D. P. Graham, "The Antihistamine Substance 2786 R.P.", Brit. J. Pharmacol., vol. 1 (1946); p. 278.

Loew, E. R. & O. Chickering, "Gastric Secretion in Dogs Treated with Histamine Antagonist, Thymoxyethyldiethylamine", Proc. Soc. Exp. Biol. and Med., vol. 48 (1941), pp. 65–68.

Nakamoto, T., M. McCroskey & H. M. Mallek, "The Role of Ascorbic Acid Deficiency in Human Gingivitis-A New Hypothesis", J. Theor. Biol., vol. 108 (1984), pp. 163–171.

Pernsteiner, C. L. & M. M. Ash, "Effect of Topical Application of Phenylephrine Hydrochloride on Hyperplastic Gingivitis", J. Peridontol., vol. 48 (1977), pp. 473–477.

Trendelenburg, U., "The Action of Histamine and 5-Hydroxytryptamine on Isolated Mammalian Atria", J. Pharmacol. & Exp. Ther., vol. 130 (1960), pp. 450–460.

*Primary Examiner*—Shep Rose
*Attorney, Agent, or Firm*—Jean R. Crosmun; Milton B. Graff, IC; David L. Suter

[57] ABSTRACT or treatment of gingivitis or periodontitis comprising topical administration, to gingival tissues of the oral cavity, of a composition comprising a safe and effective amount of a selective histamine-2 receptor antagonist compound, and oral care compositions used therefore.

13 Claims, No Drawings

USE OF H-2 ANTAGONISTS FOR TREATMENT OF GINGIVITIS

This is a continuation-in-part of application Ser. No. 07/868,805, filed on Apr. 15, 1992.

TECHNICAL FIELD

The subject invention relates to methods and compositions for the prevention and treatment of gingivitis and soft tissue aspects of periodontitis.

BACKGROUND OF THE INVENTION

"Gingivitis", as used herein, means inflammation of the gingiva (gums); it is often due to infection. Gingivitis is usually caused by the build-up of plaque, a sticky deposit of bacteria, mucous, food particles and other irritants, around the base of the teeth. It is believed that toxins produced by bacteria within the plaque irritate the gums, causing the gums to become infected, tender, and swollen. Gingivitis can also result from injury to the gums, usually from over vigorous tooth brushing or careless flossing.

Periodontitis", as used herein, means inflammation of the periodontium (the tissues that support the teeth). Chronic periodontitis is a complication of untreated gingivitis. If gingivitis is neglected, inflamed gum tissue at the base of the teeth becomes damaged and pockets form between the gums and the teeth. Plaque then collects in these pockets. The bacteria in the plaque attack the periodontal tissues, causing them to become inflamed and detached from the teeth. In advanced stages, the bacteria eventually erode the bones surrounding the teeth. However, as used herein, periodontitis is limited to the soft tissue (non-bone) aspects of the disease.

Histamine is a chemical present in cells throughout the body that is released during an allergic reaction and in instances of chronic inflammation. Histamine is one of the substances responsible for the symptoms of inflammation. It also stimulates production of acid by the stomach and narrows the bronchi (airways) in the lungs.

The effects of histamine can be counteracted by antihistaminic drugs, of which there are two well-known classes: histamine-1 receptor antagonists (H-1 antagonists) and histamine-2 receptor antagonists (H-2 antagonists). H-1 antagonists drugs are commonly used for treatment of a number of inflammatory conditions including hives and other rashes to relieve itching, swelling and redness, allergic rhinitis to relieve sneezing and runny nose, colds to dry up nasal secretions, and cough. Common H-1 antagonist drugs include chlorpheniramine, diphenhydramine, promethazine, terphenadine, trimeprazine and triprolidine.

References which disclose the use of various H-1 antagonists in oral care products or for treatment of various oral conditions are disclosed in the following references: U.S. Pat. No. 3,574,859 issued to Kosti on Apr. 13, 1971; U.S. Pat. No. 3,822,349 issued to Kosti on Jul. 2, 1974; U.S. Pat. No. 3,832,460 issued to Kosti on Aug. 27, 1974; U.S. Pat. No. 3,839,522 issued to Kosti on Oct. 1, 1974; U.S. Pat. No. 4,256,743 issued to Goldhaber on Mar. 17, 1981; U.S. Pat. No. 4,569,837 issued to Suzuki, Ikura, Noguchi, Izumizawa and Kinoshita on Feb. 11, 1986; U.S. Pat. No. 4,933,182 issued to Higashi, Kametaka, Izumi, Morisaki and Hayashi on Jun. 12, 1990; European Patent Application No. 0,241,179 of Rohto Pharmaceutical Company, published Oct. 14, 1987; European Patent Application No. 0,256,566 of ISCOFAR, published Feb. 24, 1988; European Patent Application No. 0,349,657 of Thornfeldt and Thornfeldt, published Jan. 10, 1990; British Patent Specification No. 1,045,031 of Kawakami, published Oct. 5, 1966; Canadian Patent No. 950,833 of Kosti, issued Jul. 9, 1974; Nakamoto, T., M. McCroskey and H. M. Mallek, "The Role of Ascorbic Acid Deficiency in Human Gingivitis—A New Hypothesis", *J. Theor. Biol.*, Vol. 108 (1984), pp. 163–171; and Pernsteiner, C. L. and M. M. Ash, "Effect of Topical Application of Phenylephrine Hydrochloride on Hyperplastic Gingivitis", *J. Periodontol.*, Vol. 48 (1977), pp. 473–477.

H-2 antagonists have not generally been found useful for treatment of inflammatory conditions. Instead, they are extensively used as drugs for preventing release of acid in the stomach to promote the healing of peptic ulcers and to relieve symptoms of esophagitis. Examples of well-known H-2 antagonist drugs include cimetidine, ranitidine and famotidine.

PCT Patent Application No. WO 89/04178 of Aktiebolaget Hassle, published May 18, 1989, discloses the use of H-2 antagonists for treatment of bone diseases, including the bone loss resulting from periodontal disease. The disclosed utility is achieved through systemic dosing of the H-2 antagonists. It is an object of the subject invention to provide a topical, oral treatment for gingivitis and soft tissue aspects of periodontitis.

SUMMARY OF THE INVENTION

The subject invention relates to methods for prevention or treatment of gingivitis or periodontitis comprising topical administration, to gingival tissues of the oral cavity, of a composition comprising a safe and effective amount of a selective histamine-2 receptor antagonist compound.

DETAILED DESCRIPTION OF THE INVENTION

The subject invention involves a novel use of histamine-2 (H-2 or $H_2$) receptor antagonist compounds (H-2 antagonists). As used herein, selective H-2 antagonists are compounds which block H-2 receptors, but do not have meaningful activity in blocking histamine-1 (H-1 or $H_1$) receptors.

Selective H-2 Antagonists

Histamine stimulates the contraction of smooth muscle from various organs, such as the gut and bronchi, and this effect can be suppressed by low concentrations of mepyramine—a typical antihistaminic drug. The pharmacological receptors involved in these mepyramine-sensitive histamine responses have been defined as H-1 receptors (Ash, A. S. F. and H. O. Schild, *Brit. J. Pharmacol Chemother.*, Vol. 27 (1966), p. 427, incorporated herein by reference). Histamine also stimulates the secretion of acid by the stomach (Loew, E. R. and O. Chickering, *Proc. Soc. Exp. Biol. Med.*, Vol. 48 (1941), p. 65, incorporated herein by reference), increases the heart rate (Trendelenburg, U., *J. Pharmacol.*, Vol. 130 (1960), p. 450, incorporated herein by reference), and inhibits contractions in the rat uterus (Dews, P. B. and J. D. P. Graham, *Brit. J. Pharmacol. Chemother.*, Vol. 1 (1946), p. 278, incorporated herein by reference); these actions cannot be antagonized by mepyramine and related drugs. The subject invention involves the use of compounds which specifically blockade the receptors involved in mepyramine-insensitive, non-H-1 (H-2), histamine responses, and which do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin and E. M. Parsons, "Definition and Antagonism of Histamine $H_2$, Receptors", *Nature*, Vol. 236 (Apr. 21, 1972), pp. 385-390 (Black), incorporated herein by reference, as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. (A typical reasonable dosage level is the lowest dosage level at which 90% inhibition of histamine, preferably 99% inhibition of histamine, is achieved in the above H-2 assays).

Selective H-2 antagonists include compounds meeting the above criteria which are disclosed in the following U.S. Pat. Nos. 3,751;470; 3,876,647; 3,881,016; 3,891,764; 3,894,151; 3,897,444; 3,905,984; 3,910,896; 3,920,822; 3,932,443; 3,932,644; 3,950,333; 3,968,227; 3,971,786; 3,975,530; 3,979,398; 4,000,296; 4,005,205; 4,024,271; 4,034,101; 4,035,374; 4,036,971; 4,038,408; 4,056,620; 4,056,621; 4,060,621; 4,062,863; 4,062,967; 4,070,472; 4,072,748; 4,083,983; 4,083,988; 4,084,001; 4,090,026; 4,093,729; 4,098,898; 4,104,381; 4,104,472; 4,105,770; 4,107,319; 4,109,003; 4,112,104; 4,112,234; Re 29,761; 4,118,496; 4,118,502; 4,120,966; 4,120,968; 4,120,972; 4,120,973; 4,128,658; 4,129,657; 4,133,886; 4,137,319; 4,139,624; 4,140,783; 4,145,546; 4,151,289; 4,152,443; 4,152,453; 4,153,793; 4,154,834; 4,154,838; 4,156,727; 4,157,347; 4,158,013; 4,160,030; 4,165,377; 4,165,378; 4,166,856; 4,166,857; 4,169,855; 4,170,652; 4,173,644; 4,181,730; 4,185,103; 4,189,488; 4,190,664; 4,191,769; 4,192,879; 4,197,305; 4,200,578; 4,200,760; 4,203,909; 4,210,652; 4,210,658; 4,212,875; 4,215,125; 4,215,126; 4,216,318; 4,218,452; 4,218,466; 4,219,553; 4,220,767; 4,221,737; 4,227,000; 4,233,302; 4,234,588; 4,234,735; 4,238,493; 4,238,494; 4,239,769; Re 30,457; 4,242,350; 4,242,351; 4,247,558; 4,250,316; 4,252,819; 4,255,425; 4,255,440; 4,260,744; 4,262,126; 4,264,608; 4,264,614; 4,265,896; 4,269,844; 4,271,169; 4,276,297; 4,276,301; 4,279,819; 4,279,911; 4,282,213; 4,282,221; 4,282,224; 4,282,234; 4,282,363; 4,283,408; 4,285,952; 4,288,443; 4,289,876; 4,293,557; 4,301,165; 4,302,464; 4,304,780; 4,307,104; 4,308,275; 4,309,433; 4,309,435; 4,310,532; 4,315,009; 4,317,819; 4,318,858; 4,318,913; 4,323,566; 4,324,789; 4,331,668; 4,332,949; 4,333,946; 4,336,394; 4,338,328; 4,338,447; 4,338,448; 4,341,787; 4,342,765; 4,347,250; 4,347,370; 4,359,466; 4,362,728; 4,366,164; 4,372,963; 4,374,248; 4,374,251; 4,374,839; 4,374,843; 4,375,435; 4,375,472; 4,375,547; 4,379,158; 4,380,638; 4,380,639; 4,382,090; 4,382,929; 4,383,115; 4,385,058; 4,386,099; 4,386,211; 4,388,317; 4,388,319; 4,390,701; 4,394,508; 4,395,419; 4,395,553; 4,399,142; 4,405,621; 4,405,624; 4,407,808; 4,410,523; 4,413,130; 4,426,526; 4,427,685; 4,432,983; 4,433,154; 4,435,396; 4,438,127; 4,439,437; 4,439,444; 4,439,609; 4,440,775; 4,442,110; 4,443,613; 4,447,441; 4,447,611; Re 31,588; 4,450,161; 4,450,168; 4,451,463; 4,452,985; 4,452,987; 4,458,077; 4,461,900; 4,461,901; 4,464,374; 4,465,841; 4,466,970; 4,467,087; 4,468,399; 4,470,985; 4,471,122; 4,474,790; 4,474,794; 4,476,126; 4,481,199; 4,482,552; 4,482,563; 4,482,566; 4,485,104; 4,490,527; 4,491,586; 4,492,711; 4,493,840; 4,496,564; 4,496,571; 4,499,101; 4,500,462; 4,501,747; 4,503,051; 4,507,296; 4,507,485; 4,510,309; 4,510,313; 4,514,408; 4,514,413; 4,515,806; 4,518,598; 4,520,025; 4,521,418; 4,521,625; 4,522,943; 4,523,015; 4,524,071; 4,525,477; 4,526,973; 4,526,995; 4,528,375; 4,528,377; 4,528,378; 4,529,723; 4,529,731; 4,536,508; 4,537,779; 4,537,968; 4,539,207; 4,539,316; 4,540,699; 4,543,352; 4,546,188; 4,547,512; 4,548,944; 4,550,118; 4,551,466; 4,558,044; 4,558,128; 4,559,344; 4,560,690; 4,564,623; 4,567,176; 4,567,191; 4,570,000; 4,571,394; 4,571,398; 4,574,126; 4,578,388; 4,578,459; 4,578,471; 4,584,384; 4,585,781; 4,587,254; 4,588,719; 4,588,826; 4,590,192; 4,590,299; 4,595,683; 4,595,758; 4,596,811; 4,599,346; 4,600,720; 4,600,779; 4,600,780; 4,604,465; 4,607,105; 4,607,107; 4,608,380; 4,612,309; 4,613,596; 4,613,602; 4,621,142; 4,622,316; 4,632,927; 4,632,993; 4,634,701; 4,638,001; 4,639,442; 4,639,523; 4,643,993; 4,644,006; 4,645,841; 4,647,559; 4,649,141; 4,649,145; 4,649,150; 4,650,893; 4,652,572; 4,652,575; 4,656,176; 4,656,180; 4,657,908; 4,659,721; 4,663,331; 4,665,073; 4,666,932; 4,668,673; 4,668,786; 4,670,448; 4,673,747; 4,675,406; 4,681,883; 4,683,228; 4,687,856; 4,692,445; 4,692,456; 4,692,531; 4,694,008; 4,696,933; 4,699,906; 4,699,915; 4,704,388; 4,705,873; 4,710,498; 4,716,228; 4,722,925; 4,727,081; 4,727,169; 4,728,655; 4,732,980; 4,738,960; 4,738,969; 4,738,983; 4,742,055; 4,743,600; 4,743,692; 4,745,110; 4,746,672; 4,748,164; 4,748,165; 4,749,790; 4,758,576; 4,760,075; 4,762,932; 4,764,612; 4,767,769; 4,769,473; 4,772,704; 4,777,168; 4,777,179; 4,788,184; 4,788,187; 4,788,195; 4,795,755; 4,806,548; 4,808,589; 4,814,341; 4,816,583; 4,837,316; 4,847,264; 4,851,410; 4,871,765; 4,886,910; 4,886,912; 4,894,372; 4,904,792; 4,912,101; 4,912,132; 4,937,253; 4,952,589; 4,952,591; 4,957,932; 4,965,365; 4,972,267; 4,988,828; 5,008,256; 5,021,429; 5,025,014; 5,037,837; 5,037,840; 5,047,411.

Selective H-2 antagonists include compounds meeting the above criteria which are disclosed in the following European Patent Applications: 7,326; 10,893; 17,679; 17,680; 29,303; 31,388; 32,143; 32,916; 49,049; 50,407; 57,227; 67,436; 73,971; 74,229; 79,297; 80,739; 86,647; 89,765; 103,503; 103,390; 104,611; 105,703; 112,637; 122,978; 134,096; 141,119; 141,560; 156,286; 169,969; 171,342; 172,968; 173,377; 178,503; 180,500; 181,471; 186,275; 204,148; 213,571; 277,900; 355,612; 417,751; 445,949; 454,449; 454,469.

Selective H-2 antagonists include compounds meeting the above criteria which are disclosed in World Patent Application No. 91-10,656.

Selective H-2 antagonists include compounds meeting the above criteria which are disclosed in the following U.K. Patent Applications: 1,341,590; 1,531,237; 1,565,647; 1,574,214; 2,001,624; 2,067,987; 2,094,300; 2,117,769; 2,124,622; 2,146,331; 2,149,406; 2,162,174; 2,209,163.

Selective H-2 antagonists include compounds meeting the above criteria which are disclosed in the following Belgian Patent Applications: 857,218; 857,219; 866,155; 884,820; 892,350; 905,235; 1,000,307.

Selective H-2 antagonists include compounds meeting the above criteria which are disclosed in the following German Patent Applications: 3,044,566; 3,341,750; 3,644,246.

Selective H-2 antagonists include compounds meeting the above criteria which are disclosed in the following French Patent Applications: 2,515,181; 2,531,703.

Selective H-2 antagonists include compounds meeting the above criteria which are disclosed in the following Spanish Patent Applications: 85-06,610; 86-05,244.

Selective H-2 antagonists include compounds meeting the above criteria which are disclosed in Netherlands Patent Application No. 88-02,089.

Selective H-2 antagonists include compounds meeting the above criteria which are disclosed in South African Patent Application No. 83-05,356.

Selective H-2 antagonists include compounds meeting the above criteria which are disclosed in the following Japanese Patent Applications: 53/005,180; 54/106,468; 55/053,247; 55/115,860; 55/115,877; 56/135,479; 57/054,177; 57/165,348; 57/169,452; 58/015,944; 58/072,572; 58/072,573; 58/090,569; 59/007,172; 59/010,582; 59/093,050; 59/093,051; 59/190,973; 60/197,663; 60/226,180; 60/228,465; 60/237,082; 61/063,665; 61/063,676; 61/115,072; 62/005,969; 62/126,169; 63/122,679; 63/183,563; 02/000,178; 02/056,449; 03/251,571.

Compounds cited in the following patent publications are disclosed to have H-1 and/or H-2 antagonist properties. As with compounds disclosed in the above lists of patent publications, only compounds having selective H-2 antagonist properties, as determined by the test methods described hereinabove, are included in the methods and compositions of the subject invention. The patent publications are U.S. Pat. Nos. 3,894,151; 3,954,982; 4,000,302; 4,104,382; 4,145,546; 4,154,834; 4,159,329; 4,185,103; 4,218,452; 4,220,767; 4,221,914; 4,234,588; 4,255,428; 4,305,945; 4,342,765; 4,374,836; 4,439,435; 4,496,567; 4,497,812; 4,539,207; 4,558,128; 4,634,701; 4,639,519; 4,649,141; 4,687,856; 4,723,017; 4,757,060; 4,912,119; 5,037,815; European Patent Application Nos. 24,873; 83,186; 148,096; 176,049; 320,550; 321,613; 426,479; 437,645; U.K. Patent Application Nos. 1,341,375; 1,582,527; Belgian Patent Application No. 849,810; Japanese Patent Application Nos. 59/036,674; 59/225,172; 59/225,186; 60/004,182; 60/013,768; 60/202,883.

Selective H-2 antagonists include the substituted thioalkyl-, aminoalkyl- and oxyalkyl-guanidines meeting the above criteria which are disclosed in U.S. Pat. No. 3,950,333 issued to Durant, Emmett and Ganellin on Apr. 13, 1976. Particularly preferred is cimetidine (SKF-92334), N-cyano-N'-methyl-N"-(2-(((5-methyl-1H-imidazol-4-yl)methyl)thio)ethyl)guanidine:

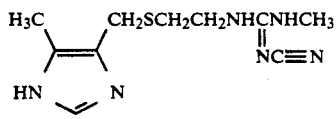

Cimetidine is also disclosed in the *Merck Index*, 11th edition (1989), p. 354 (entry no. 2279), and *Physicians' Desk Reference*, 46th edition (1992), p. 2228. Related preferred H-2 antagonists include burimamide and metiamide.

Selective H-2 antagonists include the imadazolylmethylthioethyl alkynyl guanidines meeting the above criteria which are disclosed in U.S. Pat. No. 4,112,234 issued to Crenshaw and Luke on Sep. 5, 1978. Preferred is etintidine (BL-5641, BL-5641A), N-cyano-N'-(2-(((5-methyl-1H-imidazol-4-yl)methyl)thio)ethyl)-N"-2-propynyl-guanidine.

Selective H-2 antagonists include the aminoalkyl furan derivatives meeting the above criteria which are disclosed in U.S. Pat. No. 4,128,658 issued to Price, Clitherow (and Bradshaw on Dec. 5, 1978. Particularly preferred is ranitidine, especially its hydrochloride salt (AH-19065). Ranitidine is N-(2-(((5-((dimethylamino)methyl)-2-furanyl)methyl)thio)ethyl)-N'-methyl-2-nitro-1,1-ethenediamine:

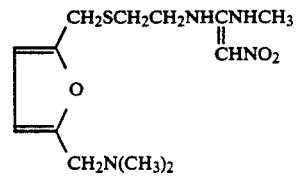

Ranitidine is also disclosed in the *Merck Index*, 11th edition (1989), p. 1291 (entry no. 8126), and *Physicians' Desk Reference*, 46th edition (1992), p. 1063. Related preferred compounds include hydroxymethyl ranitidine; ranitidine bismuth citrate (GR-122311, GR-122311X); and AH-18801, N-cyano-N'-(2-(((5-((dimethylamino)methyl)-2-furanyl)methyl)thio)ethyl)-N"-methyl guanidine.

Selective H-2 antagonists include the guanidine derivatives of imidazoles and thiazoles meeting the above criteria which are disclosed in U.S. Pat. No. 4,165,377 issued to Jones and Yellin on Aug. 21, 1979. Preferred is ICIA-5165, N-(4-(2-((aminoiminomethyl)amino)-4-thiazolyl)butyl)-N'-cyano-N"-methyl-guanidine.

Selective H-2 antagonists include the guanidine derivatives of imidazoles and thiazoles meeting the above criteria which are disclosed in U.S. Pat. No. 4,165,378 issued to Gilman, Wardleworth, and Yellin on Aug. 21, 1979. Preferred is tiotidine (ICI-125211), N-(2-(((2-((aminoiminomethyl)amino)A-thiazolyl)methyl)thio)ethyl)-N'-cyano-N"-methylguanidine.

Selective H-2 antagonists include the N-alkynyl-N'-(omega-((5-substituted-2-furyl)alkylthio)alkyl)-derivatives of N"-cyanoguanidine and of 1,1-diamino-2-(substituted)-ethylene compounds meeting the above criteria which are disclosed in U.S. Pat. No. 4,203,909 issued to Algieri and Crenshaw on May 20, 1980. Preferred is ORF-17578, N-(2-(((5-((dimethylamino)methyl)-2-furanyl)methyl)thio)ethyl)-2-nitro-N'-2-propynyl-, 1-ethene diamine.

Selective H-2 antagonists include the substituted pyrimidine compounds meeting the above criteria which are disclosed in U.S. Pat. No. 4,234,588 issued to Brown and Ife on Nov. 18, 1980. Preferred are lupitidine (SKF-93479), 2-((2-(((5-((dimethylamino)methyl)-2-uranyl)-methyl)thio)ethyl)amino)-5-, ((6-methyl-3-pyridinyl)methyl)-4(1H)-pyrimidinone; and donetidine (SKF-3574), 5-((1,2-dihydro-2-oxo-4-pyridinyl)methyl)-2-((2-(((5-(dimethylamino)methyl)-2-furanyl)methyl)thio)ethyl)amino)-4(1H)-pyrimidinone. Also preferred are related compounds SKF-93828, 2-((2-(5-((4-(dimethylaminomethyl)-2-pyridyl)methyl)thio)ethyl)amino)-5-(2-methyl-5-pyridyl)pyrimidin-4-one; and SKF- 93996, the 2-(4-(4-(dimethylaminomethyl)-2-pyridyl)-butylamino) analogue of SKF 93828.

Selective H-2 antagonists include the 3-amino-5-(4-pyridyl)-1,2,4-triazole derivatives meeting the above criteria which are disclosed in U.S. Pat. No. 4,276,297 issued to Lipinski on Jun. 30, 1981. Preferred is 3-amino-5-(2-(ethylamino)-4-pyridyl)-1,2,4-triazole.

Selective H-2 antagonists include the guanidinothazole compounds meeting the above criteria which are disclosed in U.S. Pat. No. 4,283,408 issued to Hirata, Yanagisawa, Ishii, Tsukamoto, Ito, Isoaura, and Takeda on Aug. 11, 1981. Preferred is famotidine (YM-1170, MK-208), 3-(((2-((aminoiminomethyl)amino)A-thiazolyl)methyl)thio)-N-aminosulfonyl) propanimidamide:

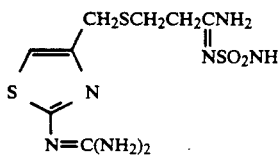

Famotidine is also disclosed in the *Merck Index*, 11th edition (1989), p. 617 (entry no. 3881), and *Physicians' Desk Reference*, 46th edition (1992), p. 1524.

Selective H-2 antagonists include the phenoxypropylamine derivatives meeting the above criteria which are disclosed in U.S. Pat. No. 4,293,557 issued to Shibata, Itaya, Yamakoshi, Kurata, Koizumi, Tarutani, Sakuma and Konishi on Oct. 6, 1981. Preferred is roxatidine (Hoe-062, TZU-9368), 2-hydroxy-N-(3-(3-(1-piperidinylmethyl)phenoxy)propyl)-acetamide; and roxatidine acetate (pifatidine, Hoe-760, TZU-0460), 2-(acetyloxy)-N-(3-(3-(1-piperidinylmethyl)phenoxy)-propyl)-acetamide:

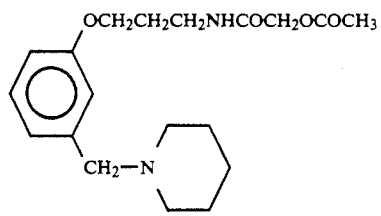

Roxatidine acetate is also disclosed in the *Merck Index*, 11th edition (1989), p. 1316 (entry no. 8252).

Selective H-2 antagonists include the 1,2,4-triazole-3,5-diamine derivatives meeting the above criteria which are disclosed in U.S. Pat. No. 4,318,913 issued to Clitherow, Bradshaw, Mackinnon, Price, Martin-Smith and Judd on Mar. 9, 1982. Preferred is lamtidine (AH-22216), 1-methyl-N5-(3-(3(1-piperidinylmethyl)phenoxy)propyl)-1H-1,2,4-triazole-3,5-diamine. Also preferred are related compounds AH-21201 and AH-21272. Selective H-2 antagonists include the 3-(hydroxy or amino)-4-substituted amino)- and 3,4-di(substituted amino)-1,2,5-thiadiazole-1-oxides and 1,1-dioxides meeting the above criteria which are disclosed in U.S. Pat. No. 4,374,248 issued to Crenshaw and Algieri on Feb. 15, 1983. Preferred are BL-6548 (ORF- 17910), N-(3-(3-((4-methyl-1-piperidinyl)methyl)phenoxy)propyl)-1,2,5-hiadiazole-3,4-diamine 1-oxide; and BMY-25271, N-(2-(((5-(dimethylamino)methyl)-2-furanyl)methyl)thio)ethyl)-1,2,5-thiadiazole-3,4-diamine 1-oxide.

Selective H-2 antagonists include the 2-guanidino-4-heteroarylthiazoles meeting the above criteria which are disclosed in U.S. Pat. No. 4,374,843 issued to LaMattina and Lipinski on Feb. 22, 1983. Preferred is zaltidine (CP-57361-01), (4-(2-methyl-1H-imidazol-4-yl)-2-thiazolyl)-guanidine.

Selective H-2 antagonists include the N-alkyl-N'-((2-(aminoalkyl)-4-thiazolylmethyl)thioalkyl)guanidines, thioureas, ethenediamines and related compounds meeting the above criteria which are disclosed in U.S. Pat. No. 4,375,547 issued to Ploch on Mar. 1, 1983. Preferred is nizatidine (LY-139037, ZL-101), N-(2-(((2-((dimethylamino)methyl)-4-thiazolyl)methyl)thio)ethyl)-N'-methyl-2-nitro-1,1-ethenediamine:

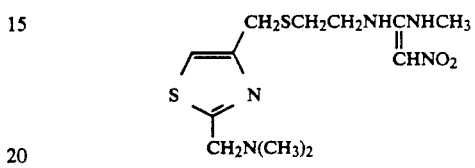

Nizatidine is also disclosed in the *Merck Index*, 11th edition (1989), p. 1052 (entry no. 6582), and *Physicians' Desk Reference*, 46th edition (1992), p. 1246.

Selective H-2 antagonists include the imidazolylphenyl amidines meeting the above criteria which are disclosed in U.S. Pat. No. 4,386,099 issued to Cereda, Donetti, Soldato and Bergamaschi on May 31, 1983. Preferred is mifentidine (DA-4577), N-(4-(1H-imidazol-4-yl)phenyl)-N'-(1-methylethyl)methanimidamide:

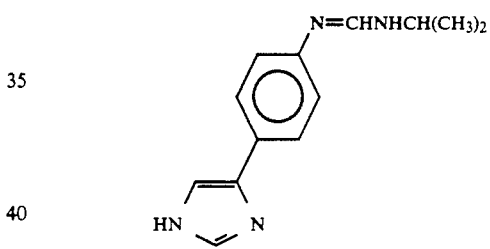

Mifentidine and its dihydrochloride salt are disclosed in the *Merck Index*, 11th edition (1989), p. 973 (entry no. 6108).

Selective H-2 antagonists include the 1-(substituted amino)-2-(amino or substituted amino)cyclobutene-3,4-diones meeting the above criteria which are disclosed in U.S. Pat. No. 4,390,701 issued to Algieri and Crenshaw on Jun. 28, 1983. Preferred are BMY-25368 (SKF-94482), 3-amino-4-((3-(3-(1-piperidinylmethyl)phenoxy)propyl)amino)-3-cyclobutene-1,2-dione and its hydrochloride salt.

Selective H-2 antagonists include the 3-(hydroxy or amino)-4-(substituted amino)- and 3,4-di(substituted amino)-1,2,5-thiadiazole 1-oxides and 1,1-dioxides meeting the above criteria which are disclosed in U.S. Pat. No. 4,394,508 issued to Crenshaw and Algiere on Jul. 19, 1983. Preferred is BL-6341A (BMY-26539), (4-(((2-((4-amino-1,2,5-thiadiazol-3-yl)amino) ethyl)thio)methyl)-2-thiazolyi)-guanidine, S-oxide.

Selective H-2 antagonists include the cycloalkylamino derivatives meeting the above criteria which are disclosed in U.S. Pat. No. 4,427,685 issued to Stemp on Jan. 24, 1984. Preferred is N-(2-(((5-dimethylaminomethyl-2-furanyl)methyl)thio)ethyl)-N'-cyclo-octyl-2-nitro-1,1'-ethenediamine.

Selective H-2 antagonists include alcohol guanidine derivatives meeting the above criteria which are disclosed in U.S. Pat. No. 4,451,463 issued to Large on May 29, 1984. Preferred is ICI-162846, 3-((imino((2,2,2-trifluoroethyl)amino)methyl)amino)-1H-pyrazole-1-pentanamide.

Selective H-2 antagonists include the thioalkylamide of nicotinic acid 1-oxide compounds meeting the above criteria which are disclosed in U.S. Pat. No. 4,474,790 issued to Nisato and Boveri on Oct.2, 1984. Preferred is ramixotidine (CM-57755), N-(2-(((5-((dimethylamino)methyl)-2-furanyl)methyl)thio)ethyl)-3-pyridinecarboxamide 1-oxide.

Selective H-2 antagonists include the benzo-fused heterocyclic compounds meeting the above criteria which are disclosed in U.S. Pat. No. 4,490,527 issued to Schiehser and Strike on Dec. 25, 1984. Preferred is Wy-45727, N-(2-(((5-dimethylamino)methyl)-2-furanyl)methyl)thio)ethyl)thieno(3,4-d)isothiazol-3-amine 1,1-dioxide.

Selective H-2 antagonists include the N-substituted nicotin amide 1-oxide compounds meeting the above criteria which are disclosed in U.S. Pat. No. 4,514,408 issued to Nisato and Boveri on Apr. 30, 1985. Preferred is SR-58042, (N-(3-(3-(3-methyl)piperidinomethyl)-phenoxy)propyl)-3-pyridinecarboxamide 1-oxide.

Selective H-2 antagonists include the 3-(amino or substituted amino)-4-(substituted amino)-1,2,5-thiadiazoles meeting the above criteria which are disclosed in U.S. Pat. Nos. 4,528,377 and 4,600,779 issued to Crenshaw and Algieri on Jul. 9, 1985 and Jul. 15, 1986, respectively. Preferred is BMY-25405, N-(3-(3-(1-piperidinylmethyl)phenoxy)propyl)-1,2,5-thiadiazole-3,4-diamine monohydrochloride.

Selective H-2 antagonists include the triazole amine derivatives meeting the above criteria which are disclosed in U.S. Pat. No. 4,536,508 issued to Clitherow, Price, Bradshaw, Martin-Smith, Mackinnon, Judd and Hayes on Aug. 20, 1985. Preferred is loxtidine (AH-23844), 1-methyl-5-((3-(3-(1-piperidinylmethyl)phenoxy)propyl)amino)-1H-1,2,4-triazole-3-ethanol.

Selective H-2 antagonists include the guanidino-heterocyclyl-phenylamidines meeting the above criteria which are disclosed in U.S. Pat. Nos. 4,548,944 and 4,645,841 issued to Bietti, Cereda, Donetti, Soldato, Giachetti and Micheletti on Oct. 22, 1985, and Feb. 24, 1987, respectively. Preferred is DA-4634, (4-(3-(((methylamino)methylene)amino)phenyl)-2-thiazolyl)-guanidine.

Selective H-2 antagonists include the amidine derivatives of 2-substituted 4-phenylimidazole compounds meeting the above criteria which are disclosed in U.S. Pat. No. 4,649,150 issued to Bietti, Cereda, Donetti, Giachetti and Pagani on Mar. 10, 1987. Preferred is bisfentidine (DA-5047), N-(1-methylethyl)-N'-(4-(2-methyl-1H-imidazol-4-yl)phenyl)-ethanimidamide.

Selective H-2 antagonists include the triazole amine compounds meeting the above criteria which are disclosed in U.S. Pat. No. 4,670,448 issued to Clitherow, Bradshaw, MacKinnon, Judd, Bays, Hayes and Pearce on Jun. 2, 1987. Preferred is sufotidine (AH-25352), 1-methyl-3-((methylsulfonyl)methyl)-N-(3-(3-(1-piperidinylmethyl)phenoxy)propyl)-1H-1,2,4-triazol-5-amine.

Selective H-2 antagonists include the sulfonamidines meeting the above criteria which are disclosed in U.S. Pat. No. 4,728,755 issued to Foguet, Anglada, Costello, Sacristan and Ortiz on Mar. 1, 1988. Preferred is ebrotidine (FI-3542), N-(((2-(((2-((aminoiminomethyl)amino)-4-hiazolyl)methyl)thio)ethyl)amino)methyiene)-4-bromo-benzenesulfonamide.

Selective H-2 antagonists include the 1,3,4-thiadiazole derivatives meeting the above criteria which are disclosed in U.S. Pat. No. 4,738,960 issued to Schickaneder, Heter, Wegner, Schunack, Szelenyi, Postius and Ahrens on Apr. 19, 1988. Preferred is HE-30-256, 1-(3-(3-(piperidinomethyl)phenoxy)-propylamino)-5-pyridin-2-sulfenamido-1,3,4-thiadiazole.

Selective H-2 antagonists include the ethylenediamine and guanidine-derivatives meeting the above criteria which are disclosed in U.S. Pat. No. 4,738,983 issued to Emig, Scheffler, Thiemer and Weischer on Apr. 19, 1988. Preferred is D-16637, N-(2(((5-((tricyclo(2.2.1.0)hept-3-ylamino)methyl-2-furanyl)methyl)-thio)ethyl)-N-methyl-2-nitro-1,1-ethenediamine HCl.

Selective H-2 antagonists include the 4-aminomethyl-pyridyl-2-oxy derivatives meeting the above criteria which are disclosed in U.S. Pat. Nos. 4,912,101 and 4,977,267 issued to Hirakawa, Kashiwaba, Matsumoto, Hosoda, Sekine, Isowa, Yamaura, Sekineland Nishikawa on Mar. 27 and Dec. 11, 1990, respectively. Preferred is FRG-8813, N-(4-(4-(piperidinomethyl)-pyridyl-2-oxy)-(Z)-2-butenyl)-2-(furfurylsulfinyl)acetamide.

Selective H-2 antagonists include the alkylamide derivatives meeting the above criteria which are disclosed in U.S. Pat. No. 4,837,316, issued to Sekine, Hirakawa, Kashiwaba, Yamaura, Harada, Katsuma, Matsumoto, Sekine and Isowa on Jun. 6, 1989. Preferred is FRG-8701, N-(3-(3-(piperidinomethyl)phenoxy)propyl)-2-(furfurylsulfinyl)acetamide.

Selective H-2 antagonists include the N,N'-disubstituted guanidine compounds meeting the above criteria which are disclosed in U.K. Patent Specification No. 1,531,237 of Durant, Ganellin and Parsons published on Nov. 8, 1978. Preferred is impromidine.

Selective H-2 antagonists include the 3,4-diamino-1,2,5-thiadiazole compounds meeting the above criteria which are disclosed in European Patent Application No. 0,040,696 of Baldwin, Bolhofer, Lumma, Amato, Karady and Weinstock, published Dec. 2, 1981. Preferred is L-643728, 4-amino-3-(2-(5-(dimethylaminomethyl)-2-furanylmethylthio)ethylamino)-5-thoxycarbonyl-isothiazole-1,1-dioxide.

Selective H-2 antagonists include the 2-substituted amino-4(1H)-pyrimidone derivatives meeting the above criteria which are disclosed in European Patent Application No. 0,186,275 of Yanagisawa, Ohta, Takagi and Takeuchi, published Jul. 2, 1986. Preferred is HB-408, 5-butyl-6-methyl-2-(3-(3-(piperidinomethyl)phenoxy)-propylamino)pyrimidin-4(1H)-one.

Selective H-2 antagonists include the active compounds meeting the above criteria which are disclosed in Hoffman, J. M., A. M. Pietruszkiewicz, C. N. Habecker, B. T. Phillips, W. A. Bolhofer, E. J. Cragoe, M. L. Torchiana, W. C. Lumma and J. J. Baldwin, "Conformational Requirements for Histamine $H_2$-Receptor Inhibitors: A Structure-Activity Study of Phenylene Analogues Related to Cimetidine and Tiotidine", *J. Med. Chem.*, Vol. 26 (1983), p. 140–144. Preferred is L-643441, N-(3-(3-(1-piperidinylmethyl)phenoxy)-propyl)-1,2,5-thiadiazole-3,4-diamine 1-oxide.

Selective H-2 antagonists include the active compounds meeting the above criteria which are disclosed in Borchers, V. A., H. Engler, I. Szelenyi and Selective H-2 antagonists include the active compounds meeting the above criteria which are disclosed in Borchers, V. A., H. Engler, I. Szelenyi and W. Schunack, "Synthese und H$_2$-antihistaminische Wirkung N,N'-bismidazo(substituierter Thioharnstoffe, Cyanoguanidine und 2-Nitro-1,1-ethendiamine", *Arzneim. Forsch.*, Vol. 32 (1982), pp. 1509-1512. Preferred is N-cyano-N',N''-bis(2-((5-methyl-4-imidazolyl)methylthio)ethyl)guanidine.

Selective H-2 antagonists include the active compounds meeting the above criteria which are disclosed in Elz, V.S. and W. Schunak, "H$_2$-antagonistische Aktivitat Impromidin-analoger Cyanoguanidine", *Arzneim.-Forsch.*, Vol. 38(I), No. 1 (1988), pp. 7-10. Preferred is N-cyano-N'-(2-(4,5,6,7-tetrahydrobenzimidazol-2-yl)ethyl)-1-N''-(2-((5-methylimidazol-4-yl)methyl thio)ethyl)guanidine.

Selective H-2 antagonists include the active compounds meeting the above criteria which are disclosed in Borella, L., J. Russell, T. J. Rimele, D. Grimes, A. Failli and G. N. Mir, "Antisecretory and Antiulcer Activities of a Potent New Histamine H$_2$-Receptor Antagonist with an Intermediate Duration of Action", *Arzneim. Forsch.*, Vol. 38(I), No. 3 (1988), pp. 366-372. Preferred is AY-29315, 4-(dimethylamino)-N-(2-((4-((3-(3-(1-piperidinylmethyl)phenoxy) propyl)amino)-1,2,5-hiadiazol-3-yl)amino)ethyl)butanamide S-oxide.

Selective H-2 antagonists include the active compounds meeting the above criteria which are disclosed in Muramatsu, M., Y. Isobe, I. Arai, H. Hirose-Kijima, C. Usuki-Ito, H. Nagai, M. Aihara and S. Otomo, "Effects of the New H$_2$-Receptor Antagonist 3-Amino-4-(4-(4-(1-piperidinomethyl)-2-Pyridyloxy)-cis-2-butenylamino)-3-cyclobutene-1,2-dione Hydrochloride on Gastric Acid Secretion and Ulceration", *Arzneim. Forsch.*, Vol. 40(I), No. 1 (1990), pp. 49-54. Preferred is IT-066, 3-imino-4-(4-(4-(1 -piperidinomethyl)-2-pyridoxy)-cis-2-butenylamino)-3-cyclobutene-1,2-dione HCl.

Selective H-2 antagonists include the active compounds meeting the above criteria which are disclosed in Katz, L. B., A. J. Tobia and D. A. Shriver, "Effects of ORF-17583, Other Histamine H$_2$-Receptor Antagonists and Omeprazole on Gastric Acid Secretory States in Rats and Dogs", *The Journal of Pharmacology and Experimental Therapeutics*, Vol. 242 (1987), pp. 437-442. Preferred is ORF-17583 (BL-6217), N-(2-(((5-((dimethylamino)methyl)-2-furanyl)methyl)thio)ethyl)-N'-methyl-1,2,5-thiadiazole-3,4-diamine 1-oxide.

Selective H-2 antagonists include the active compounds meeting the above criteria which are disclosed in Nielsen, S. T., P. Dove, G. Palumbo, A. Sandor, C. Buonato, G. Schiehser, A. Santilli and D. Strike, "Two H$_2$-Receptor Antagonists as Inhibitors of Gastric Acid Secretion", *Fed. Proc.*, Vol. 43 (1984), Abst. No. 4617. Preferred are Wy-45086, N-(3-(3-((1-piperidinyl)methyl)phenoxy)propyl)- 3-benzisothiazoleamine 1,1-dioxide and Wy-45253, N-(3-(3-(1-pyrrolidinylmethyl)-phenoxy)propyl)-1,2-benzisothiazol-3-amine 1,1-dioxide HCl.

Selective H-2 antagonists include the active compound meeting the above criteria which are disclosed in Goto, Y., M. Yamada and T. Nagata, "Antisecretory Activity of a Novel H-2 Antagonist, IK-82029, Is Specific to Histamine-2 Receptors in the Rat", *Gastroenterology*, Vol. 90 (1986), p. 1435, IK-82029:

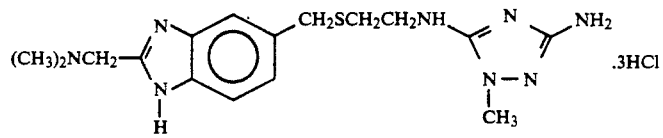

Selective H-2 antagonists include the active compounds meeting the above criteria which are disclosed in Tsuriya, Y., H. Matsukawa, H. Aoky and M. Seye, "The Pharmacological Properties of 2-N-(3-(3-(1-piperidinomethyl)-phenoxy)propyl)amino-5-amino-1,3,4-thiadiazole (TAS), a New Histamine H$_2$-Receptor Antagonist: Comparison with Ranitidine and Cimetidine", *Japan J. Pharmacol.*, Vol. 63(Suppl.) (1984), p. 90P-91P. Preferred is TAS, N,N-(3-(1-piperidinomethyl)phenoxypropyl)amino-5-amino-1,3,4-thiadiazole.

Selective H-2 antagonists include the active compounds meeting the above criteria which are disclosed in Oshita, M., K. Morikawa, T. Aratani, H. Kato and Y. Ito, "Pharmacological Studies of 2-(3-(3-(1-Piperidinylmethyl)phenoxy)propylamino)-4(3H)-Quinazolinone (NO-794), a New Histamine H$_2$-Receptor Antagonist", *Japan J. Pharmacol.*, Vol. 42 (1986), pp. 229-235. Preferred is NO-794, 2-((3-(3-(1-piperidinylmethyl)phenoxy)propyl)amino-4(3H)-quinazolinone.

Selective H-2 antagonists include the active compounds meeting the above criteria which are disclosed in Nishida, A., K. Miyata, I. Yanagisawa, M. Takeda, T. Kamato, H. Ito, H. Yuki, M. Yamano, R. Tsutsumi and K. Honda, "Effects of YM-14471, a Potent and Long-Lasting Histamine H$_2$-Receptor Antagonist, on Gastric Acid Secretion in Rats and Dogs", *Japan J. Pharmacol.*, Vol. 55 (Suppl 1) (1991), Abstract P497). Preferred is YM-14471, 2-(2-(2-diaminomethyleneamino)thiazol-4-ylmethylthio)ethyl)-5-(3-(diethylamino) propyl)-6-methyl-pyrimidin-4(1H)-one 3HCl.

H-2 antagonists include the active compounds meeting the above criteria which are disclosed in Ueda, I., K. Ishii, K. Shinozaki, M. Seiki, H. Arai and M. Hatanaka, "Synthesis and Pharmacological Properties of N-[3-{3-(1-Piperidinylmethyl)phenoxy)propyl]-2-(2-hydroxyethylthio)acetamide and Related Compounds as Antiulcer Agents. I", *Chem. Pharm. Bull.*, Vol. 38(11) (1990), p. 3035-3041. Preferred is N-(3-(3-(1-piperidinylmethyl)phenoxy) propyl)-2-(2-hydroxyethylthio)acetamide.

Selective H-2 antagonists include the active compounds meeting the above criteria which are disclosed in *Dialog* File 3128, Pharmaprojects Database entry no. 00015689, Mar. 21, 1991, PJB Publications Ltd., Richmond, Surrey, UK. Preferred is Z-300. Selective H-2 antagonists include the active compound meeting the above criteria which is disclosed in Nelson, S. T., "H$_2$-receptor Antagonist and Gastric Acid Antisecretory Properties of Wy-45,662", *Agents and Actions*, Vol. 19(3/4) (1986), pp. 158-163: Wy-45662, N-(3-(3-(1-piperidinylmethyl)phenoxy)propyl)-thieno(3,4-d)isothiazol-3-amine 1,1-dioxide.

Selective H-2 antagonists include the active compounds meeting the above criteria which are disclosed in Michael, J. D., J. D. Coombes, S. J. Cousins, D. B.

Norris, T. J. Rising, B. C. Ross and A. Steward, "Synthesis of 4-Alkyl-1,2,4,6-thiatriazine 1,1-dioxide derivatives: Potent New Histamine H-2 Antagonists", 190th ACS (Chicago), 1985, MEDI 33. Preferred is tuvatidine (HUK-978), (4-(((2-((5-amino-4-methyl-4H-1,2,4,6-thiatriazin-3-yl)amino)ethyl) thio)methyl)-2-thiazolyl)-guanidine S,S-dioxide.

Selective H-2 antagonists include N-(3-(3-(1-piperidinyl)phenoxy) propyl)thieno(3,4-d)-isothiazol-3-amine-1,1-dioxide, meeting the above criteria, as disclosed in Santilli, A. A., A. C. Scotese, R. L. Morris, G. A. Schiehser, D. M. Teller, S. T. Nielsen and D. P. Strike, "Syntheses and Gastric Acid Antisecretory Properties of the $H_2$-Receptor Antagonist N-[3-[3-(1-Piperidinylmethyl)phenoxy]propyl]thieno[3,4-d]isothiazol-3-amine 1, 1-Dioxide and Related Derivatives, *J. Med. Chem.*, Vol. 31 (1988), pp. 1479–1486.

Selective H-2 antagonists include FCE-23067, 2-guanidine-5-(N-isopropylcarbamoyl)-4,5,6,7-tetrahydrothiazole(5,4-c)pyridine, meeting the above criteria.

Selective H-2 antagonists include CRC-1970, N-cyano-N'-methyl-N"-(2(((2-(((4-methyl-5-oxazolyl)methyl)thio)ethyl)-guanidine, meeting the above criteria.

Selective H-2 antagonists include RGW-2568 (WHR-2568), N5-(3-((2,3-dihydro-1-(1-piperidinyl)-1 H-inden-4-yl)oxy)propyl)-methyl-1H-1,2,4-triazole-3,5-diamine, meeting the above criteria.

Selective H-2 antagonists include the following compounds meeting the above criteria: 5,6-substituted 4-pyrimidone compounds disclosed in Spengler, J.-P., K. Wegner and W. Schunack, "$H_2$-Antihistaminics. 20. Structure-Activity Relationships in $H_2$-Receptor Antagonists Containing a 4-Pyrimidone Moiety", *Agents and Actions*, Vol. 14, No. 3/4 (1984), pp. 566–568; 3- and 2-indole derivatives disclosed in Tecle, H., L. Robichaud, and C. F. Schwender, "Potential Histamine $H_2$-Receptor Blockers. 3- and 2-indole Derivatives as Immobile Analogues of Tautomeric Forms of Cimetidine", *J. Med. Chem.*, Vol. 24 (1981), pp. 1095–1097; benzylhistamine compounds disclosed in Emmett, J. C., G. J. Durant, C. R. Ganellin, A. M. Roe and J. L. Turner, "Potential Histamine $H_2$-Receptor Antagonists. 4. Benzylhistamines", *J. Med. Chem.*, Vol. 25 (1982), pp. 1168–1174; (imidazolylphenyl)guanidine, imidazolylbenzamidine, and (imidazolylphenyl)formamidine compounds disclosed in Donetti, A., E. Cereda, E. Bellora, A. Gailazzi, C. Bazzano, P. Vanoni, P. Del Soldato, R. Micheletti, F. Pagani and A. Giachetti, "(Imidazolylphenyl)formamidines. A Structurally Novel Class Of Potent Histamine $H_2$ Receptor Antagonists", *J. Med. Chem.*, Vol. 27 (1984), pp. 380–386; N-cyano and N-carbamoyl amidine derivatives disclosed in Yanagisawa, I., Y. Hirata and Y. Ishii, "Histamine $H_2$ Receptor Antagonists. 1. Synthesis of N-Cyano and N-Carbamoyl Amidine Derivatives and Their Biological Activities", *J. Med. Chem.* Vol. 27 (1984), pp. 849–857; biaryl pyridyl compounds disclosed in Lipinski, C. A., J. L. LaMattina and L. A. Hohnke, "Pseudosymmetry and Bioisosterism in Biaryl Pyridyl Competitive Histamine $H_2$-Receptor Antagonists", *J. Med. Chem.*, Vol. 28 (1985), pp. 1628–1636; cimetidine analogs disclosed in Young, R. C., G. J. Durant, J. C. Emmett, C. R. Ganellin, M. J. Graham, R. C. Mitchell, H. D. Prain and M. L. Roantree, "Dipole Moment in Relation to $H_2$ Receptor Histamine Antagonist Activity for Cimetidine Analogues", *J. Med. Chem.*, Vol. 29 (1986), pp. 44–49; biaryl imidazolyl and triazolyl compounds disclosed in Lipinski, C. A., J. L. LaMattina P. J. Oates, "Bioisosteric Prototype Design of Biaryl Imidazolyl and Triazolyl Competitive Histamine $H_2$-Receptor Antagonists", *J. Med. Chem.*, Vol. 29 (1986), pp. 2154–2163; zwitterionic analogues of cimetidine disclosed in Young, R. C., C. R. Ganellin, M. J. Graham, R. C. Mitchell, M. L. Roantree and Z. Tashma, "Zwitterionic Analogues of Cimetidine as $H_2$ Receptor Antagonists", *J. Med. Chem.*, Vol. 30 (1987), pp. 1150–1156; N-substituted thieno(3,4-d)isothiazol-3-amine 1,1-dioxides and analogs disclosed in Santilli, A. A., A. C. Scotese, R. L. Morris, G. A. Schiehser, D. M. Teller, S. T. Nielsen and D. P. Strike, "Syntheses and Gastric Acid Antisecretory Properties of the $H_2$-Receptor Antagonist N-(3-(3-(1-Piperidinylmethyl)phenoxy)-propyl)thieno(3,4-d)isothiazol-3-amine 1,1-Dioxide and Related Derivatives", *J. Med. Chem.*, Vol. 31 (1988), pp. 1479–1486; pyrimidine and reduced pyrimigine analogues disclosed in El-Badry, O. M. and E. E. Knaus, "Pyridine and Reduced Pyridine Analogues as Histamine $H_2$-Receptor Antagonists", *Eur. J. Med. Chem. Chim. Ther.*, Vol. 20, No. 5 (1985), pp. 403–407; pyrimidine and reduced pyrimidine analogues of Pyridine Analogues of Ranitidine as Histamine $H_2$-Receptor Antagonists", *Eur. J. Med. Chem. Chim. Ther.*, Vol. 20, No. 5 (1985), pp. 409–413; diaminofurazan compounds disclosed in Sorba, G., R. Calvino, A. Defilippi, A. Gasco and M. Orsetti, "Potential Histamine $H_2$-Receptor Antagonists: Diaminofurazan, a New Urea Equivalent Group", *Eur. J. Med. Chem. - Chim. Ther.*, Vol. 20, No. 6 (1985), pp. 571–574; ranitidine analogues containing 5(6)substituted benzimidazole moieties disclosed in Sorba, G., A. Garrone, A. Serafino, A. Gasco and M. Orsetti, "Potential Histamine $H_2$-Receptor Antagonists: Ranitidine Analogues Containing 2-Amino-5(6)-Substituted-Benzimidazole Moieties", *Eur. J. Med. Chem. - Chim. Ther.*, Vol. 21, No. 5 (1986), pp. 391–395; cimetidine and impromidine congeners disclosed in Sterk, G. J., H. Van Der Goot H. Timmerman, "Studies on Histaminergic Compounds VI. Synthesis and Structure - Activity Relationships of a Series of Cjmetidine and impromidine Congeners", *Eur. J. Med. Chem.*, Vol. 22 (1987), pp. 427–432; pyridine and reduced pyridine analogues of cimetidine disclosed in El-Badry, O. M., E. E. Knaus and J. H. McNeill, "Pyridine and Reduced Pyridine Analogues of Cimetidine as Histamine $H_2$-Receptor Antagonists", *Euro. J. Med. Chem.*, Vol. 22 (1987), pp. 579–582; N'-substituted thiourea, cyanoguanidine and dithiooxamide compounds disclosed in Barzen, R. and W. Schunack, "Synthese und $H_2$-Antihistaminische Wirkung N,N'-Substituierter Thioharnstoffe, Cyanoguanidine und Dithiooxamide", *Arch. Pharm. (Weinheim)*, Vol. 314 (1981), pp. 617–622; ketene N,N-acetal compounds disclosed in Barzen, R. and W. Schunack, "Keten-N,N-Acetale Mit $H_2$-Antihistaminischer Wirkung", Vol. 315 (1982), pp. 680–684; guanidinothiazole compounds disclosed in Trumm, V. K.-A. and W. Schunack, "Guanidinothiazole Mit $H_2$-Antihistaminischer Wirkung", *Arzneim.-Forsch./Drug Res.*, Vol. 33(1), No. 2 (1983), pp. 188–190, and Spengier, V. J.-P and W. Schunack, "Razemische Guanidinothiazole Mit $H_2$-Antihistaminischer Wirkung", *Arzneim-Forsch./Drug Res.*, Vol. 33(1), No. 3 (1983), pp. 377–380; N,N'-bisheteroaryl substituted cyanoguanidine and 2-nitro-1,1-ethenediamine compounds disclosed in Borchers, V. A., S. Postius, I. Szelenyi and W. Schunack, "Synthese und $H_2$-Antihistaminische Wirkung N,N'-Bisheteroaryl-Substituierter Cyanoguanidine und 2-Nitro-1,1-Ethendiamine", *Arzneim.-Forsch./Drug Res.*, Vol. 34(II), No. 7 (1984), pp. 751-754.

All of the above patents and other references which disclose H-2 antagonists and methods of testing H-2 and H-1 antagonists are hereby incorporated herein by reference.

Compositions

One aspect of the subject invention is compositions comprising a safe and effective amount, preferably from about 0.001% to about 20%, more preferably from about 0.01% to about 15%, more preferably still from about 0.1% to about 10%, still more preferably from about 1% to about 5%, of a H-2 antagonist, and a pharmaceutically-acceptable topical, oral carrier.

The pH of the compositions of the subject invention for which pH can be measured is preferably from about 2 to about 11, more preferably from about 4 to about 10, more preferably still from about 5 to about 9.

"Safe and effective amount", as used herein, means an amount of a substance high enough to provide a significant positive modification of the condition to be treated, but low enough to avoid serious side effects (at a reasonable benefit/risk ratio), within the scope of sound medical judgement. A safe and effective amount of the substance will vary with the particular condition being treated, the severity of the condition, the duration of the treatment, the nature of concurrent therapy, and like factors.

"Topical, oral carrier", as used herein, denotes a carrier for the H-2 antagonist which results in a composition which is administered topically to the oral cavity, held therein for a period of time, and then is largely expectorated rather than being swallowed. Such compositions include toothpastes, tooth gels, tooth powders, mouthwashes, mouthsprays, prophylaxis pastes, dental treatment solutions, oral gels, chewing gums, controlled-release drug delivery systems for placement in the periodontal pocket, and the like.

Components of the topical, oral carrier are suitable for administration to the oral cavity of a human or lower animal and are compatible with one another and the other components, especially the H-2 antagonist, used in an oral composition of the subject invention. The term "compatible" as used herein, means that the components of the compositions are capable of being commingled with one another, in a manner such that there is no interaction which would substantially reduce the efficacy of the oral composition under ordinary use conditions. Preferred topical, oral carriers thus provide the desired characteristics for toothpastes, tooth gels, tooth powders, mouthwashes, mouthsprays, prophylaxis pastes, dental treatment solutions, oral gels, chewing gums, subgingival fibers, and the like. The topical, oral carriers of the subject invention comprise components typically used in such compositions which are well known to a skilled practitioner. Such components include, but are not limited to, anticaries agents, antiplaque agents, anticalculus agents, anti-inflammatory agents, dental abrasives, surfactants, flavoring agents, sweetening agents, binders, humectants, thickening agents, buffering agents, preservatives, coloring agents and pigments, ethanol and water.

Water is an optional component of the topical, oral carriers of the compositions of the subject invention. Water employed in the preparation of the commercially suitable compositions should preferably be of low ion content and free of organic impurities. Water preferably comprises from about 2% to about 99%, more preferably from about 20% to about 95% of the compositions of the subject invention. When in the form of toothpastes, the compositions preferably are from about 2% to about 45%, more preferably from about 30% to about 40%, water. Mouthwashes are preferably from about 45% to about 95%, more preferably from about 75% to about 90%, water.

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, and resinous abrasive materials.

A class of preferred abrasives for use in the subject compositions is the particulate thermo-setting polymerized resins as described in U.S. Pat. No. 3,070,510 issued to Cooley and Grabenstetter on Dec. 25, 1962. Suitable resins include, for example, melamines, phenolics, ureas, melamine-ureas, melamine-formaldehydes, urea-formaldehydes, melamine-urea-formaldehydes, cross-linked epoxides, and cross-linked polyesters.

Silica dental abrasives are also preferred in the compositions of the subject invention. The silica abrasive polishing material generally has an average particle size ranging between about 0.1 and about 30 microns, preferably between about 5 and about 15 microns. The abrasive can be precipitated silica or silica gels such as the silica xerogels described in U.S. Pat. No. 3,538,230 issued to Pader and Wiesner on Mar. 2, 1970, and in U.S. Pat. No. 3,862,307 issued to DiGuilio on Jan. 21, 1975. Preferred are the silica xerogels marketed under the tradename Syloid ® by the W. R. Grace and Co., Davison Chemical Division. Preferred precipitated silica materials are those marketed by the J. M. Huber Corporation under the tradename Zeodent ®, particularly the silica carrying the designation Zeodent 119 ®. These silica abrasives are described in U.S. Pat. No. 4,340,583 issued to Wason on Jul. 29, 1982.

Mixtures of abrasives can be used. All of the above patents regarding dental abrasives are incorporated herein by reference. The total amount of abrasive in dentifrice compositions of the subject invention preferably range from about 10% to about 70% by weight; toothpastes preferably contain from about 10% to about 50% by weight of abrasives. Solution, mouthspray, mouthwash and oral gel compositions of the subject invention typically contain no abrasive.

Flavoring agents are preferred in the topical, oral carriers of the compositions of the subject invention in order to make them more palatable. Typical flavoring agents include menthol, oil of wintergreen, oil of peppermint, oil of spearmint, oil of sassafras, and oil of clove. If present, flavoring agents are generally included in the subject compositions in amounts of from about 0.04% to about 2% by weight.

Sweetening agents are also preferred in the topical, oral carriers of the compositions of the subject invention in order to make them more palatable. Typical sweetening agents include sugars, such as sucrose, glucose, dextrose and levulose, saccharin salts, thaumatin, aspartame, D-tryptophan, dihydrochalcones, acesulfame and cyclamate salts, especially sodium cyclamate and sodium saccharin. If present, sweetening agents are generally included in the subject compositions in amounts of from about 0.01% to about 5% by weight.

Another optional component of the topical, oral carriers of the compositions of the subject invention is a humectant. The humectant serves to keep toothpaste compositions from hardening upon exposure to air, and to give compositions a moist feel to the mouth. Certain humectants can also impart desirable sweetness of flavor to the subject compositions. The humectant, on a pure humectant basis, generally comprises from about 0% to about 70%, preferably from about 2% to about 55%, by weight of the compositions herein. Suitable humectants for use in compositions of the subject invention include edible polyhydric alcohols such as glycerin, sorbitol, xylitol, polyethylene glycol, and propylene glycol, especially sorbitol and glycerin.

Buffering agents are another optional component of the topical, oral carrier of the compositions of the subject invention. The buffering agents serve to retain the pH of the compositions within the preferred range. The buffering agent generally comprises from about 0% to about 1 0%, preferably from about 0.2% to about 5%, by weight of the compositions herein. Suitable buffering agents for use in compositions of the subject invention include soluble phosphate salts.

Other optional components of the topical, oral carriers of the compositions of the subject invention are preservatives. The preservatives prevent microbial growth in the compositions. Suitable preservatives include methylparaben, propylparaben, benzoates and ethanol. If the preservative is ethanol, it generally comprises from 0% to about 35%, preferably from about 5% to about 15%, of the compositions. Other preservatives generally comprise from about 0% to about 5%, preferably from about 0.1% to about 2%, by weight of the compositions.

Binders and thickening agents may be used in the topical, oral carriers of the compositions of the subject invention, particularly in toothpaste compositions. Preferred binders and thickening agents include, for example, carrageenan (e.g., Irish moss, Viscarin TP-5 which is an iota carrageenan), lo cellulose derivatives (e.g., hydroxyethyl cellulose, sodium carboxymethyl cellulose, sodium carboxymethyl hydroxypropyl cellulose), carboxyvinyl polymers (carbomers), natural gums (e.g., gum karaya, gum arabic, gum tragacanth), polysaccharide gums (e.g., xanthan gum), fumed silica, and colloidal magnesium aluminum silicate. If present, these binders and thickening agents are generally present in the compositions of the subject invention in amounts of from about 0.1% to about 5%.

Compositions of the subject invention may also contain a surfactant. Suitable surfactants are those which are reasonably stable and preferably form suds through the pH range of the compositions. Surfactants useful as sudsing agents may be soaps, and anionic, nonionic, cationic, zwitterionic and amphoteric organic synthetic detergents, and compatible mixtures thereof. Surfactants of these types are described more fully in U.S. Pat. No. 3,959,458 issued to Agricola, Briner, Granger and Widder on May 25, 1976, incorporated herein by reference. Such surfactants are generally present in the compositions of the subject invention at a level of from 0% to about 10%, preferably from about 0.2% to about 5%. Surfactants may also be used as solubilizing agents to help retain sparingly soluble components, e.g., some flavoring agents, in solution. Surfactants suitable for this purpose include polysorbates and poloxamers.

Compositions of the subject invention may also include one or more anticalculus agents, on the condition that they are compatible with the H-2 antagonist. Anticalculus agents which may be useful in the compositions of the subject invention include, but are not limited to, pyrophosphates or polyphosphates such as those disclosed in U.S. Pat. No. 4,590,066 issued to Parran and Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Benedict, Bush and Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker and Gloxhuber on Oct. 26, 1976 and U.S. Pat. No. 4,877,603 issued to Degenhardt and Kozikowski on Oct. 31, 1989; all of these patents are incorporated herein by reference. Preferred anticalculus agents include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate. If present, the anticalculus agents generally comprise from about 0.2% to about 13%, preferably from about 0.4% to about 6% of the compositions of the subject invention.

The compositions of the subject invention may also comprise an anticaries agent. Preferred anticaries agents are water-soluble fluoride ion sources. Fluoride ions also generally help stabilize pyrophosphate (generally an anticalculus agent) in the oral cavity, thus enhancing the benefits provided by any soluble pyrophosphate included in the compositions. The number of such fluoride ion sources is great and includes those disclosed in U.S. Pat. No. 3,535,421 issued Oct. 20, 1970 to Briner and Widder, incorporated herein by reference. Preferred fluoride ion source materials include: sodium fluoride, potassium fluoride, stannous fluoride, and sodium monofluorophosphate and mixtures thereof. Sodium fluoride is the preferred fluoride source. The amount of the fluoride ion source in the oral compositions of the subject invention, if present, is preferably sufficient to provide from about 0.005% to about 0.35%, more preferably from about 0.05% to about 0.3% of fluoride ions in the compositions.

Antimicrobial antiplaque agents can also optionally be present in the oral compositions of the subject invention, on the condition that they are compatible with the H-2 antagonist. Such agents may include, but are not limited to, triclosan, 5-chloro-2-(2,4-dichlorophenoxy)-phenol, as described in *The Merck Index*, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpy chloride (CPC) (*Merck Index*, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as sodium peroxide, hydrogen peroxide, and magnesium monoperphalate and its analogs as described in U.S. Pat. No. 4,670,252; and analogs and salts of the above antimicrobial antiplaque agents. If present, lo the antimicrobial antiplaque agents generally comprise from about 0.1% to about 5% by weight of the compositions of the subject invention.

Antiinflammatory agents can also be present in the oral compositions of the subject invention, on condition that they are compatible with the H-2 antagonist. Such agents may include, but are not limited to, non-steroidal antiinflammatory agents such as ketorolac, flurbiprofen, ibuprofen, naproxen, indomethacin, aspirin, ketoprofen, piroxicam and meclofenamic acid. If present, the antiinflammatory agents generally comprise from about 0.001% to about 5% by weight of the compositions of the subject invention.

Nutrients can also be present in the oral compositions of the subject invention, on condition that they are compatible with the H-2 antagonist. Such agents may include folate, retinoids (Vitamin A), Vitamin C, Vitamin E and zinc. If present, the nutrients generally comprise from about 0.001% to about 10% by weight of the compositions of the subject invention.

Preferred compositions of the subject invention are in the form of dentifrices, such as toothpastes, tooth gels and tooth powders. Components of such toothpastes and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anticalculus agent (from about 0.1% to about 13%), and an antimicrobial antiplaque agent (from about 0.1% to about 5%). Tooth powders, of course, contain substantially all non-liquid components.

Preferred dentifrice compositions comprise from about 0.1% to about 10%, more preferably from about 0.5% to about 5%, more preferably from about 0.8% to about 3%, more preferably from about 1 % to about 2.5%, more preferably still from about 1% to about 1.5%, also more preferably from about 1.5% to about 2% of a H-2 antagonist and a dentifrice carrier.

Other preferred compositions of the subject invention are mouthwashes and mouthsprays. Components of such mouthwashes and mouthsprays typically include one or more of water (from about 45% to about 95%), ethanol (from about 0% to about 25%), a humectant (from 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and lo mouthsprays may also include one or more of an anticaries agent (from about 0.05% to about 0.3% as fluoride ion), an anticalculus agent (from about 0.1% to about 3%), and an antimicrobial antiplaque agent (from about 0.1% to about 5%).

Preferred mouthwash and mouthspray compositions comprise from about 0.01% to about 1%, preferably from about 0.05% to about 0.5%, more preferably from about 0.08% to about 0.3%, more preferably from about 0.1% to about 0.25%, more preferably still from about 0.1% to about 0.15%, also more preferably from about 0.15% to about 0.2% of a H-2 antagonist and a mouthwash or mouthspray carrier.

Other preferred compositions of the subject invention are dental solutions. Components of such dental solutions generally include one or more of water (from about 90% to about 99%), preservative (from about 0.01% to about 0.5%, thickening agent (from 0% to about 5%), flavoring agent (from about 0.04% to about 2%), sweetening agent (from about 0.1% to about 3%), and surfactant (from 0% to about 5%).

Preferred dental solution compositions comprise from about 0.01% to about 1%, preferably from about 0.05% to about 0.5%, more preferably from about 0.08% to about 0.3%, more preferably from about 0.1% to about 0.25%, more preferably still from about 0.1% to about 0.15%, also more preferably from about 0.15% to about 0.2% of a H-2 antagonist and dental solution carrier.

Oral gel compositions typically include one or more of water (from 0% to about 99%), a humectant such as glycerin, (from 0% to about 99%), a thickening agent (from about 0.1% to about 5%), a flavoring agent (from about 0.04% to about 2%), and a sweetening agent (from about 0.01% to about 0.5%).

Preferred oral gel compositions comprise from about 0.1% to about 10%, more preferably from about 0.5% to about 5%, more preferably from about 0.8% to about 3%, more preferably from about 1% to about 2.5%, more preferably still from about 1% to about 1.5%, also more preferably from about 1.5% to about 2% of a H-2 antagonist and an oral gel carrier.

Chewing gum compositions typically include one or more of a gum base (from about 50% to about 99%), a flavoring agent (from about 0.04% to about 2%) and a sweetening agent (from about 0.01% to about 20%).

Preferred chewing gum compositions comprise from about 0.1% to about 10%, more preferably from about 0.5% to about 5%, more preferably from about 0.8% to about 3%, more preferably from about 1% to about 2.5%, more preferably still from about 1% to about 1.5%, also more preferably from about 1.5% to about 2% of a H-2 antagonist and chewing gum carrier.

Other preferred compositions of the subject invention are controlled-release drug delivery systems for placement in the periodontal pocket. Such systems include, but are not limited to, the cellulose hollow fibers disclosed in U.S. Pat. No. 4,175,326 issued to Goodson on Nov. 27, 1979; the ethylcellulose films disclosed in U.S. Pat. No. 4,568,535 issued to Loesche on Feb. 4, 1986; the absorbable putty-like material disclosed in U.S. Pat. No. 4,568,536 issued to Kronenthal, Maftei and Levy on Feb. 4, 1986; the biodegradable microspheres and matrix disclosed in U.S. Pat. No. 4,685,883 issued to Jernberg on Aug. 11, 1987; the microparticle or microcapsule suspensions disclosed in U.S. Pat. No. 4,780,320 issued to Baker on Oct. 25, 1988; and the polymeric devices disclosed in European Patent Application No. 0,140,766 of Goodson, published May 8, 1985; these patents are incorporated herein by reference. Such controlled-release delivery systems generally include a solid matrix, usually of polymeric material, loaded with one or more active agents, the matrix entraping the H-2 antagonist. Typically, the active agents diffuse from the solid material into the periodontal pocket over time.

Preferred controlled-release drug delivery systems comprise from about 0.001% to about 50%, more preferably from about 0.01% to about 25%, more preferably still from about 0.1% to about 15%, still more preferably from about 1% to about 1 0%, of a H-2 antagonist and a controlled-release carrier.

Methods of Use

Another aspect of the subject invention involves methods of preventing or treating gingivitis and the soft tissue aspects of periodontitis for those in need of such prevention or treatment. Preferred methods are by topical application of compositions comprising a safe and effective amount of H-2 antagonist, to the mucosal tissues of the oral cavity, especially the gingival mucosa. Such compositions are described hereinabove. Preferred are methods for treating gingivitis or the soft tissue aspects of periodontitis by topical application, to gingival mucosa afflicted with the disease, of a safe and effective amount of H-2 antagonist.

Although selective H-2 antagonists are not generally known as anti-inflammatory agents, the treatment of gingivitis and the soft tissue aspects of periodontitis by the topical application of a H-2 antagonist surprisingly reduces inflammation caused by the disease.

While the methods of the subject invention are not limited to a particular mechanism of action, it is believed that the activity of H-2 antagonists in preventing and treating gingivitis and the soft tissue aspects of periodontitis involves the following mechanism. The local recruitment of polymorphonuclear (PMN) leukocytes and production of antibodies are important to achieving a protective host tissue response against plaque bacteria and their products. This protection is important to the prevention of the development of gingivitis and periodontitis. Also, histamine has a suppressive effect on both PMN leukocyte function and development of antibody responses to foreign antigens. These suppressive effects of histamine are mediated via H-2 receptors. Thus, the local release of histamine as a consequence of gingival inflammation and local antigen-antibody complexes suppresses local PMN leukocyte function and/or antibody responses. These effects are relieved by the topical application of H-2 antagonist to the gingival tissues. In turn, topical application of H-2 antagonist to the gingival tissues results in the reestablishment of a competent local host tissue response and prevention of the development of gingivitis and periodontitis.

A preferred method of the subject invention involves the contact of a composition of the subject invention with oral cavity soft tissue afflicted with gingivitis or periodontitis for at least about 15 seconds, preferably from about 20 seconds to about 10 minutes, more preferably from about 30 seconds to about 60 seconds. The method often involves expectoration of most of the composition following such contact, preferably followed by rinsing, e.g., with water. The frequency of such contact is preferably from about once per week to about four times per day, more preferably from about thrice per week to about thrice per day, more preferably still from about once per day to about twice per day. The period of such treatment typically ranges from about one day to a lifetime.

The following examples are provided as illustrations of the composition and methods of the subject invention, but are not limitations of the scope of the subject invention.

EXAMPLES 1 AND 2

Examples of toothpaste and tooth gel compositions of the subject invention are made by conventional processes by mixing the following:

| Ingredients | Example 1 (Wt. %) | Example 2 (Wt. %) |
|---|---|---|
| Sorbitol | 41.44 | 35.00 |
| Saccharin Sodium | 0.46 | 0.20 |
| FD & C Blue (1% soln) | — | 0.05 |
| Precipitated Silica | 20.00 | 25.00 |
| Sodium Fluoride | 0.24 | 0.24 |
| Flavor | 1.00 | 1.50 |
| Purified Water | q.s. | q.s. |
| Sodium Alkyl Sulfate | 4.00 | 1.20 |
| Trisodium Phosphate | 1.45 | — |
| Monosodium Phosphate | 0.59 | — |
| Carbopol 940 | 0.30 | 0.25 |
| Xanthan Gum | 0.48 | 0.65 |
| Titanium Dioxide | 0.53 | — |
| Cimetidine | 2.00 | — |
| Mifentidine | — | 0.50 |

EXAMPLES 3 AND 4

Examples of mouthwash compositions of the subject invention are made by conventional processes by mixing the following:

| Ingredients | Example 3 (Wt. %) | Example 4 (Wt. %) |
|---|---|---|
| Sorbitol | 37.20 | 37.20 |
| Glycerine | 19.00 | 19.00 |
| Polyethylene Glycol 600 | 3.00 | 3.00 |
| Sodium Saccharin | 0.17 | 0.17 |
| Precipitated Silica | 20.00 | 20.00 |
| Sodium Fluoride | 0.24 | 0.24 |
| Flavor | 0.90 | 0.90 |
| Purified Water | q.s. | q.s. |
| Sodium Alkyl Sulfate | 1.00 | 1.00 |
| Monobasic Sodium Phosphate, Monohydrate | 5.00 | 5.00 |
| Fumed Silica | 2.00 | 2.00 |
| Carboxymethylcellulose | 0.30 | 0.30 |
| Titanium Dioxide | 0.50 | 0.50 |
| Famotidine | 2.50 | — |
| Nizatidine | — | 4.00 |

EXAMPLES 5 AND 6

Examples of toothpaste and tooth gel compositions of the subject invention are made by conventional processes by mixing the following:

| Ingredients | Example 5 (Wt. %) | Example 6 (Wt. %) |
|---|---|---|
| Sorbitol | 17.23 | 17.23 |
| Silica | 23.41 | 23.41 |
| Sodium Alkyl Sulfate | 4.00 | 4.00 |
| Xanthan Gum | 0.60 | 0.60 |
| Titanium Dioxide | 0.50 | — |
| Carbopol 940 | 0.20 | 0.20 |
| Glycerin | 9.00 | 9.00 |
| Sodium Fluoride | 0.24 | 0.24 |
| Tetrapotassium Pyrophosphate | 6.38 | 6.38 |
| Sodium Acid Pyrophosphate | 2.10 | 2.10 |
| Tetrasodium Pyrophosphate | 2.05 | 2.05 |
| Polyethylene Glycol 600 | 3.00 | 3.00 |
| Peppermint Oil | 0.80 | — |
| Spearmint Oil | — | 1.00 |

-continued

| Ingredients | Example 5 (Wt. %) | Example 6 (Wt. %) |
| --- | --- | --- |
| Saccharin Sodium | 0.46 | 0.46 |
| FD & C Blue (1% sol'n) | 0.05 | 0.05 |
| Cimetidine | — | 1.00 |
| Ranitidine | 2.00 | — |

EXAMPLES 7 AND 8

Examples of mouthwash compositions of the subject invention are made by conventional processes by mixing the following

| Ingredients | Example 7 (Wt. %) | Example 8 (Wt. %) |
| --- | --- | --- |
| Cetylpyridinium Chloride | 0.045 | 0.045 |
| Domiphen Bromide | 0.005 | 0.005 |
| Purified Water | q.s. | q.s. |
| Alcohol (Standard Denatured No. 40) | 16.25 | 8.50 |
| Glycerin | 10.00 | 7.50 |
| Poloxamer 407 | 0.20 | 0.20 |
| Sodium Hydroxide | 0.003 | 0.003 |
| Sodium Benzoate | 0.05 | 0.54 |
| Benzoic Acid | 0.005 | 0.003 |
| Tween 80 | 0.03 | 0.12 |
| FD & C Green (1% sol'n) | 0.04 | 0.12 |
| FD & C Blue (1% sol'n) | 0.003 | — |
| FD & C Yellow (1% sol'n) | — | 0.001 |
| Saccharin | 0.06 | 0.08 |
| Peppermint Oil | 0.14 | — |
| Spearmint Oil | — | 0.12 |
| Cimetidine | 0.30 | — |
| Ranitidine | — | 0.20 |

EXAMPLES 9 AND 10

Examples of mouthwash compositions of the subject invention are made by conventional processes by mixing the following

| Ingredients | Example 9 (Wt. %) | Example 10 (Wt. %) |
| --- | --- | --- |
| Famotidine | 0.05 | — |
| Roxatidine Acetate | — | 1.0 |
| Ethanol | 12.00 | 15.00 |
| Glycerin | 10.00 | 12.00 |
| Dibasic Sodium Phosphate Heptahydrate | 0.07 | 0.48 |
| Saccharin Sodium | 0.08 | 0.08 |
| Monobasic Sodium Phosphate Monohydrate | 2.03 | 1.82 |
| Polysorbate 80 | 0.33 | 0.33 |
| FD & C Blue (1% Soln) | 0.02 | 0.02 |
| Flavor | 0.15 | 0.15 |
| Purified Water | q.s. | q.s. |

EXAMPLE 11

An example of a dental solutio of the subject invention is made by mixing the following:

| Ingredients | Example 11 (Wt. %) |
| --- | --- |
| Water | q.s. |
| Ranitidine | 1.00 |
| Flavor | 0.10 |
| Polysorbate 80 | 0.25 |
| Saccharin Sodium | 0.05 |
| Methylparaben | 0.20 |
| Propylparaben | 0.10 |

EXAMPLE 12

An example of an oral gel composition of the subject invention is made by mixing the following:

| Ingredients | Example 12 (Wt. %) |
| --- | --- |
| Hydroxyethyl Cellulose | 2.50 |
| Purified Water | q.s. |
| Sodium Fluoride | 0.09 |
| Saccharin Sodium | 0.05 |
| FD & G Green No. 3 (1% sol'n) | 0.01 |
| Ranitidine | 1.00 |

EXAMPLE 13

An example of a controlled-release polymer composition for placement in a periodontal pocket is as follows:

| Ingredient | Example 13 (Wt %) |
| --- | --- |
| Ethyl Cellulose, Type N22 from Hercules, Inc. | 90 |
| Mifentidine | 10 |

The ethyl cellulose is dissolved in chloroform and then the mifentidine is added. The resulting mixture is cast on a glass plate. After evaporation of the chloroform, the residual film is removed from the plate and cut into pieces.

EXAMPLE 14

An example of a putty-like controlled-release composition for placement in a periodontal pocket is made by mixing the following:

| Ingredient | Example 14 (Wt. %) |
| --- | --- |
| Calcium Stearate | 40 |
| Dextran | 29 |
| Castor Oil | 28 |
| Nizatidine | 3 |

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method for prevention or treatment of gingivitis or soft tissue aspects of periodontitis comprising topical administration, to gingival tissues of the oral cavity, of a fluoride toothpaste of a composition comprising a safe and effective amount of a selective H-2 antagonist.

2. The method of claim 1 wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408.

3. The method of claim 1 wherein the selective H-2 antagonist is selected from the group consisting of cimetidine, ranitidine, famotidine, roxatidine, nizatidine and mifentidine.

4. The method of claim 1 wherein the selective H-2 antagonist is selected from the group consisting of cimetidine, ranitidine, famotidine, and nizatidine.

5. The method of claim 1 wherein the selective H-2 antagonist is cimetidine.

6. The method of claim 1 wherein the selective H-2 antagonist is ranitidine.

7. The method of any of claims 1, 4, 5 and 6 wherein the composition comprises from about 0.01% to about 10% of the selective H-2 antagonist.

8. A fluoride toothpaste or toothpaste or tooth gel composition comprising:
(a) a safe and effective amount of a selective H-2 antagonist; and
(b) a toothpaste or tooth gel carrier comprising a dental abrasive, a surfactant, a humectant, a flavoring or sweetening agent, and
(c) a safe and effective amount of a fluoride anticaries agent water.

9. The composition of claim 8 wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-5727, SR-58042, BMY-25405, loxtidine, DA-4634, bisfentidine, sufotidine, ebrotidine, HE-30-256, D-16637, FRG-8813, FRG-8701, impromidine, L-643728, and HB-408.

10. The compositions of claim 9 wherein the selective H-2 antagonist is selected from the group consisting of cimetidine, ranitidine, famotidine, roxatidine, nizatidine and mifentidine.

11. The composition of claim 9 wherein the selective H-2 antagonist is selected from the group consisting of cimetidine, ranitidine, famotidine and nizatidine.

12. The composition of claim 9 wherein the selective H-2 antagonist is cimetidine.

13. The composition of claim 9 wherein the selective H-2 antagonist is ranitidine.

* * * * *